United States Patent [19]

Hershberger et al.

[11] 4,436,815

[45] Mar. 13, 1984

[54] METHOD FOR STABILIZING AND SELECTING RECOMBINANT DNA CONTAINING HOST CELLS

[75] Inventors: Charles L. Hershberger, New Palestine; Paul R. Rosteck, Jr., Beech Grove, both of Ind.

[73] Assignee: Eli Lilly and Company, Indianapolis, Ind.

[21] Appl. No.: 325,511

[22] Filed: Nov. 27, 1981

[51] Int. Cl.³ .................. C12N 15/00; C12N 1/20; C12N 1/00; C12P 21/00; C12P 21/02; C07H 21/04

[52] U.S. Cl. .................. 435/172; 435/68; 435/70; 435/253; 435/317; 536/27

[58] Field of Search ............ 435/172, 317, 253, 68, 435/70; 536/27

[56] References Cited

U.S. PATENT DOCUMENTS 4,356,270 10/1982 Itakura ............................ 435/317
4,366,246 12/1982 Riggs ................................ 435/68

OTHER PUBLICATIONS

Bolivar et al., Gene 2:75 (1977).
Crea et al., PNAS 75:5765 (1978).
ATCC Quarterly Newsletter, ATCC, 12301 Parklawn Drive, Rockville, Md., p. 7.
Honigman et al., Gene 13, 289–298 (1981).
Hallewell et al., Gene 9, 27–47 (1980).
Miozzari et al., J. Bacteriol. 133, 1457 (1978).
Lewin, *Gene Expression-3*, John Wiley & Sons, Inc., New York., 1977, pp. 352–380.
Hayes: *The Genetics of Bacteria and Their Viruses*, 2nd Ed., J. Wiley & Sons, New York, 1968, p. 193.

*Primary Examiner*—Thomas G. Wiseman
*Assistant Examiner*—James Martinell
*Attorney, Agent, or Firm*—Gerald V. Dahling; Arthur R. Whale

[57] ABSTRACT

An improved method for stabilizing and selecting host cells containing recombinant DNA which expresses a functional polypeptide and the novel organisms and cloning vectors for the practice thereof.

27 Claims, 9 Drawing Figures

Restriction Site and Functional Map of Plasmid pIA7 Δ 4 Δ 1
(5270 bp) Arrows Indicate Direction of Transcription

Restriction Site and Functional Map of Plasmid pIB7Δ4Δ1
(5295 bp) Arrows Indicate Direction of Transcription

Restriction Site and Functional Map of Plasmid pPR3
(7740 bp) Arrows Indicate Direction of Transcription

Restriction Site and Functional Map of Plasmid pPR12
(5062 bp) Arrows Indicate Direction of Transcription

Restriction Site and Functional Map of Plasmid pPR17
(5970 bp) Arrows Indicate Direction of Transcription

Restriction Site and Functional Map of Plasmid pPR18
(5995 bp) Arrows Indicate Direction of Transcription

Figure 7
Thymosin Alpha I Gene

```
         1   2   3   4   5   6   7   8   9   10  11  12  13  14  15  16  17  18  19  20  21  22  23  24  25  26  27  28
         Met Ser Asp Ala Ala Val Asp Thr Ser Ser Glu Ile Thr Thr Lys Asp Leu Lys Glu Lys Lys Glu Val Val Glu Glu Ala Glu Asn                    stop stop
EcoRI
←—T₁—→
AATTCATGTCTGATGCTGCTGTTGATACTTCTTCTGAGATTACTACTAAA|GATCTTAAGGAGAAGAAGGAAGTTGTCGAAGAGGCTGAGAACTAATAG
    ←——T₂——→      ←——T₄——→             ←——T₉——→     ←——T₁₀——→        ←——T₁₁——→       ←——T₁₂——→
         ←——T₃——→
GTACAGACTACGACGACAACTATGAAGAAGACTCTAATGATGATTT CTAG|AATTCCTCTTCTTCCTTCAACAGCTTCTCCGACTCTTGATTATCCTAG
    ←——T₅——→        ←——T₇——→                BglII      ←——T₁₃——→       ←——T₁₄——→       ←——T₁₅——→    ←T₁₆→
        ←——T₆——→                                                                                    BamHI
```

Synthesis Procedure for Fragment T₁₅

Construction Route for Plasmid pThα1

METHOD FOR STABILIZING AND SELECTING RECOMBINANT DNA CONTAINING HOST CELLS

SUMMARY OF THE INVENTION

The invention is an improved selective system that provides a means for stabilizing and selecting recombinant DNA host cells through the use of a lethal chromosomal marker which is repressed by a gene borne on a recombinant DNA cloning vector. This is particularly important because recombinant DNA cloning vectors such as plasmids, are often rapidly lost from bacterial populations and industrial scale fermentations may require more than $10^{16}$ cells. Therefore, once the recombininant DNA coding for the desired product is inserted in a plasmid, it is desirable if not essential, that the microorganism culture containing the plasmid be stabilized so that all the cells comprising the culture will contain the desired plasmid. This is crucial since recombinant plasmids with foreign DNA are notoriously unstable and often more than 90% of the cells in a population may not contain the recombinant plasmid after a culture has been grown overnight. Consequently the productive capacity is dramatically reduced because expression of desired genes is possible only in those cells which retain the plasmid.

Very few effective methods have been described for stabilization of recombinant plasmids and all have serious disadvantages. One method involves incorporating antibiotic resistance genes into recombinant plasmids and then adding the appropriate antibiotic to the culture medium. Cells retaining the plasmid with the antibiotic resistance gene are selected for and those which lose the plasmid are selected against and are therefore eliminated. The major disadvantage of this approach is that it requires production scale growth of antibiotic resistant bacteria, use of an expensive antibiotic in the fermentation medium, and subsequent purification to remove the antibiotic from the desired product.

Complementation of an auxotrophic mutation on the chromosome is the other known method for stabilization of recombinant plasmids. This approach severely restricts the composition of the fermentation medium and requires fermentation in a medium that does not contain the required nutrient of the host bacteria. Moreover, syntrophism may allow cells to continue growth after loss of the plasmid. Therefore, both types of selection depend on specific manipulation of the media. Such restrictions increase the cost of fermentation and limit the options available for improving productivity.

Alternative selections which are independent of media composition, which provide for maintenance of the recombinant DNA cloning vector under all conditions of fermentation, and which allow for enhanced biosynthesis of a polypeptide product, are urgently needed. Cell suicide is adaptable to satisfy this need in that suicidal cells containing a lethal marker on a chromosome and a repressor or complementing gene on a recombinant DNA cloning vector can be constructed. Cells constructed to these specifications will die if they lose the vector. The present invention improves this principle by insuring, not only that substantially all viable cells in a culture will carry the desired recombinant cloning vector, but also that the expression of genes contained in the cloning vector is enhanced.

Enhanced expression of product genes and also the absence of plasmid segregation are particularly advantageous and serve to distinguish the present invention from other selective systems which also involve the bacteriophage λcI repressor. Such a selective system, comprising cloning vectors which comprise both the cI repressor gene containing ~2.5 kb BglII restriction fragment of bacteriophage λ and also a gene which expresses a functional polypeptide, is disclosed in U.S. Pat. application Ser. No. 275,088, filed June 18, 1981. Although the gene which codes for the functional polypeptide is expressed, the particular plasmid construction therein disclosed shows some segregation and also does not allow for enhanced and optimum production of product. The improved method of the present invention solves these problems by affording an excellent means for stabilizing and selecting recombinant DNA containing host cells while concurrently maximizing gene expression and biosynthesis of a functional polypeptide.

For purposes of the present invention and as defined herein, a recombinant DNA cloning vector is any agent, including but not limited to plasmids, bacteriophages, and viruses, consisting of a DNA molecule to which one or more additional DNA segments can or have been added.

Transformation, as defined herein, is the introduction of DNA into a recipient host cell that changes the genotype and consequently results in a heritable change in the recipient cell.

A transformant, as defined herein, is a recipient cell that has undergone transformation.

A repressor, as defined herein, is a gene which is located on a recombinant DNA cloning vector and which represses and prevents expression of a lethal or conditionally lethal gene in a chromosome of a host cell.

A functional polypeptide, as defined herein, is a recoverable bioactive entirely heterologous polypeptide or precursor, a recoverable bioactive polypeptide comprised of a heterologous polypeptide and a portion or whole of a homologous polypeptide, a recoverable bioinactive fusion polypeptide comprised of a heterologous polypeptide and a bioinactivating homologous polypeptide which can be specifically cleaved, or a bioactive polypeptide the presence of which can be detected.

A fused gene product, as defined herein, is a recoverable heterologous polypeptide which is fused with a portion or whole of a homologous polypeptide.

A marker, as defined herein, is a gene or combination of genes of known function and location in a chromosome, recombinant DNA cloning vector, or virus.

$Ap^r$, as defined herein, designates the ampicillin resistant phenotype.

$Ap^s$, as defined herein, designates the ampicillin sensitive phenotype.

$Tc^r$, as defined herein, designates the tetracycline resistant phenotype.

$Tc^s$, as defined herein, designates the tetracycline sensitive phenotype.

DETAILED DESCRIPTION OF THE INVENTION

Figure 1:
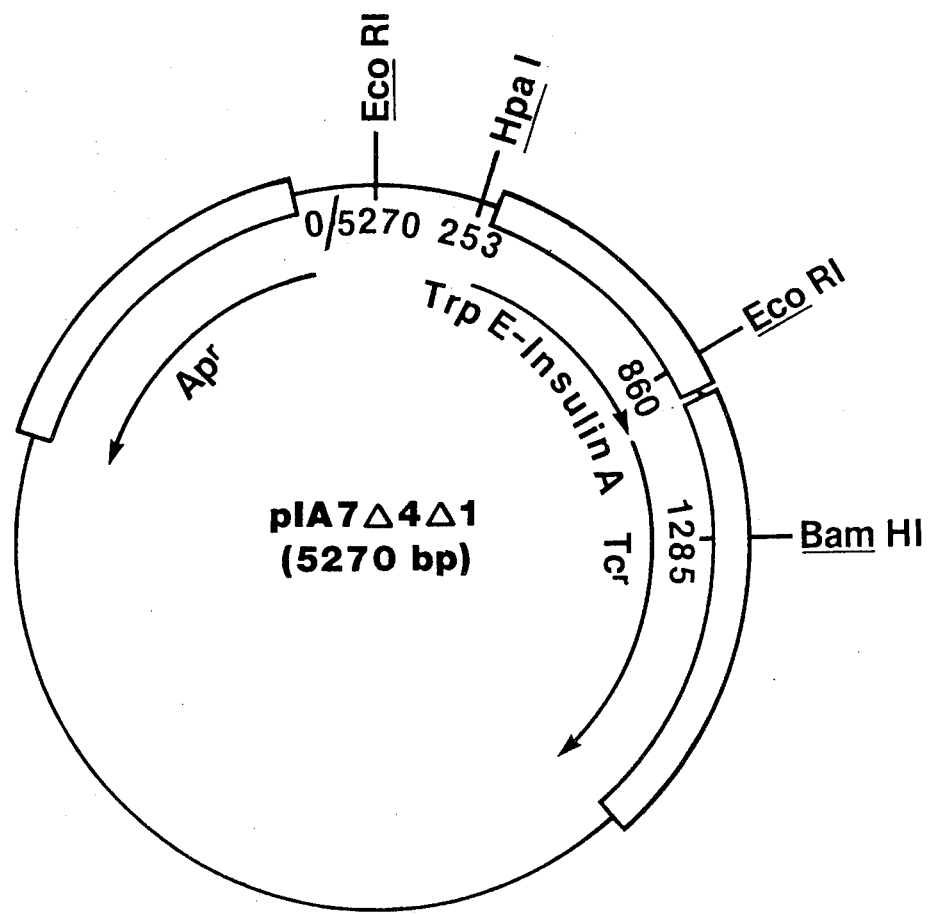

The present invention is an improvement of the method for stabilizing and selecting host cells containing recombinant DNA in which host cells are transformed with a recombinant DNA cloning vector which contains both the ~2.5 kb BglII cI repressor containing restriction fragment of Bacteriophage λ and a gene which expresses a functional polypeptide, and in which the transformed host cells are lysogenized with a lysogenic organism containing a marker which is lethal or conditionally lethal in the host cells but which is repressed in the transformed host cell by the repressor gene contained in the recombinant DNA cloning vector, wherein the improvement comprises transforming the host cells with a recombinant DNA cloning vector comprising:

(a) the PstI-HincII cI repressor containing restriction fragment of bacteriophage λ; and (b) a gene which expresses a functional polypeptide; subject to the limitation that the recombinant DNA cloning vector contains a replicon and a promoter which are not sensitive to the repressor, and subject to the further limitation, that when the transformed host cells are lysogenized with a lysogenic organism containing a gene which is conditionally lethal, the resulting host cells are cultured under restrictive conditions. The invention further comprises novel cloning vectors and organisms.

As discussed above, the present invention can be used for the growth of cultures which produce products coded by recombinant DNA. Without an effective selective system, many cells in such cultures lose the desired plasmid and consequently production of the desired product is markedly reduced. The present invention not only insures that substantially all viable cells in a culture will carry the recombinant DNA cloning vector, but it also enhances gene expression such that greater amounts of a functional polypeptide are biosynthesized. Therefore, the present invention is particularly advantageous and is distinguished by the lack of plasmid segregation, the enhanced level of gene expression, and the significantly larger quantities of functional polypeptide produced when the improved, as compared to the non-improved, method is in place.

The present invention is particularly versatile since it can be applied to the production of any substance where synthesis is determined by a recombinant DNA cloning vector. A preferred recombinant DNA cloning vector is the plasmid although bacteriophage and other vectors useful for illustrating the present invention will be apparent to those skilled in the art. Since the usefulness of the present invention is independent of the genes that express a functional polypeptide, the invention can be used with recombinant strains that carry one or more genes of commercial value. Furthermore, the previously described enhancement of gene expression is not limited to any particular product gene. Thus, the improved method of the present invention is advantageous for producing any functional polypeptide or other gene product using recombinant DNA techniques.

The interaction of bacteriophage λ with $E.$ $coli$ K12 is employed to illustrate the applicability of cell suicide for maintaining and stabilizing recombinant DNA host cells. Bacteriophage λ is a temperate bacteriophage that follows either of two mutually exclusive cycles when infecting $E.$ $coli$ K12. In the lytic phase the bacteriophage DNA replicates autonomously, directs synthesis and assembly of bacteriophage components, and kills the cells concommitant with the release of mature bacteriophage. In the lysogenic phase the bacteriophage is integrated into the host's chromosome as a prophage, replicates as a marker on the chromosome, and blocks synthesis of bacteriophage components. A bacteriophage gene, λcI, codes for a repressor that maintains the lysogenic state and blocks expression of genes for bacteriophage components and maturation. If the repressor is inactivated or removed from the cell, the prophage educts from the chromosome, enters the lytic cycle, and kills the cell. Bacteriophage with a defective λcI gene cannot maintain the lysogenic state and are lethal to the cell unless a functional repressor is provided from an alternate source. In an illustrative embodiment of the present invention, λcI90 is employed as a repressor dependent prophage and a cI gene, contained in a restriction fragment and cloned into a recombinant DNA cloning vector, serves as the functional repressor.

More particularly, the improved selective system and usefulness of this invention can be shown by cloning the plasmid pIA7Δ4Δ1 ~1.3 kb EcoRI-BamHI restriction fragment, which contains the trpE-insulin A chain gene, onto novel plasmid pPR12. This is done in such a way as to delete the plasmid pPR12 ~0.4 kb EcoRI-BamHI segment. Plasmid pPR12 is generally useful as a vector since any desirable DNA fragment can be used in place of the plasmid pIA7Δ4Δ1 ~1.3 kb restriction fragment. Plasmid pPR12 is constructed by inserting the plasmid pPR3 ~0.9 kb PstI-HincII restriction fragment, which contains the bacteriophage λcI857 repressor, onto plasmid pBR322. Plasmid pPR3 is constructed by inserting the 2.5 kb BglII fragment of bacteriophage λcI857 into the unique BamHI restriction site of plasmid pIB7Δ4Δ1. The 2.5 kb BglII restriction fragment of bacteriophage λcI857, in addition to containing the cI repressor gene, also contains the rex gene and part of the cro gene. Surprisingly, deletion of the cro gene and most of the rex gene from the cI repressor gene containing restriction fragment greatly increases and enhances genetic expression and thus production of functional polypeptide. An especially preferred cro and rex deleted λcI containing restriction fragment, used herein to exemplify the present invention, is the ~0.9 kb PstI-HincII restriction fragment of plasmid pPR3. A restriction site and functional map of each of plasmids pIA7Δ4Δ1, pIB7Δ4Δ1, pPR3, and pPR12 is presented in FIGS. 1-4 of the accompanying drawings.

Plasmid pIA7Δ4Δ1, as illustrated herein, contains the $E.$ $coli$ tryptophan promoter, antibiotic resistance markers, and a gene which expresses a fused gene product comprising a portion of the $E.$ $coli$ trp E protein fused with the A polypeptide chain of human insulin. Plasmid pIB7Δ4Δ1 is similar except that the gene which expresses the fused gene product comprises a portion of the trp E protein fused with the B, rather than the A, polypeptide chain of human insulin.

Plasmid pIA7Δ4Δ1 is derived from plasmid pBR322 and is constructed according to the procedure disclosed in Example 1A-I herein. With regard to conventions, the symbol "Δ" connotes a deletion. Thus, for example, reference to a plasmid followed by, "ΔEcoRI-XbaI" describes the plasmid from which the nucleotide sequence between EcoRI and XbaI restriction enzyme sites has been removed by digestion with those enzymes. For convenience, certain deletions are denoted by number. Thus, beginning from the first base pair ("bp") of the EcoRI recognition site which precedes the gene for tetracycline resistance in the parental plasmid pBR322, "Δ1" connotes deletion of bp 1-30 (ie, ΔEcoRI-HindIII) and consequent disenabling of the tetracycline promoter/operator system; "Δ2" connotes deletion of bp 1-375 (ie, ΔEcoRI-BamHI) and consequent removal of both the tetracycline promoter/operator and a portion of the structural gene which encodes tetracycline resistance; and "Δ4" connotes deletion of bp ~900-~1500 from the trp operon fragment eliminating the structural gene for the trp D polypeptide.

Figure 5:
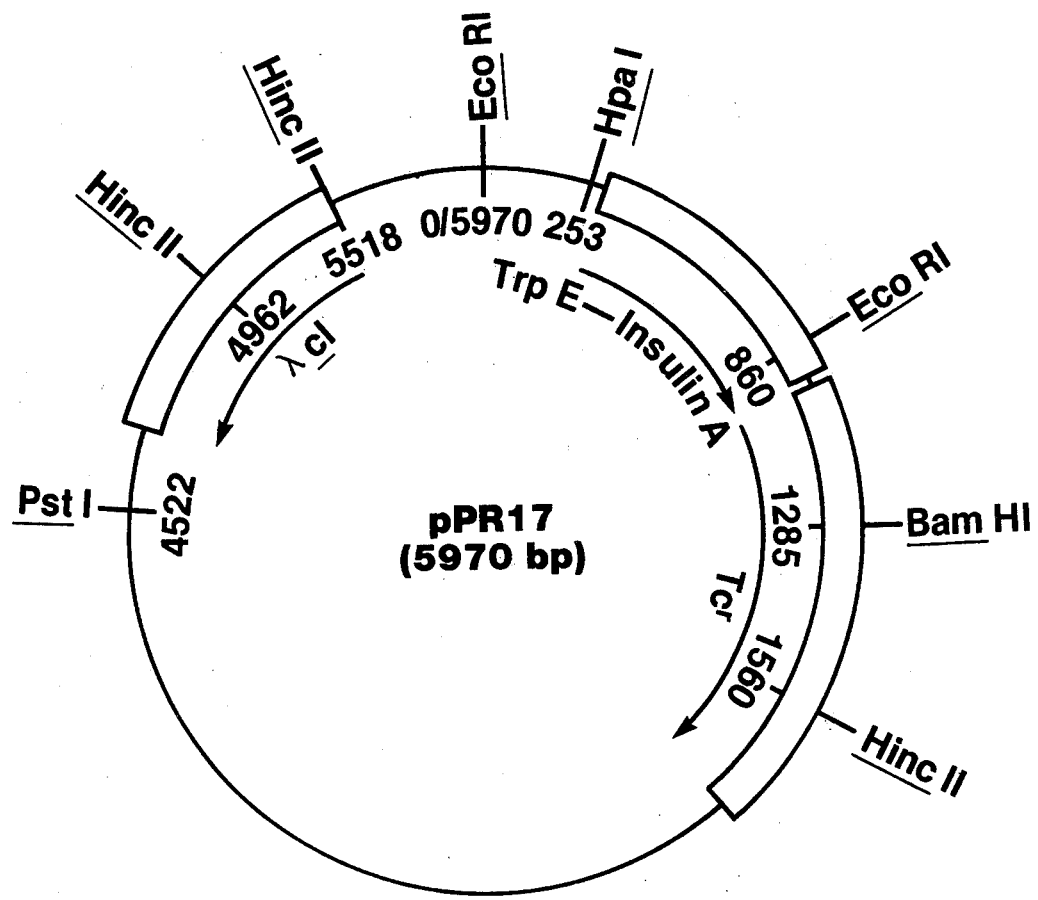

The cloning of the ~1.3 kb EcoRI-BamHI trp E-insulin A chain gene containing restriction fragment of plasmid pIA7Δ4Δ1 onto the ~4.7 kb EcoRI-BamHI restriction fragment of plasmid pPR12, hereinafter designated pPR12Δ2, results in the novel plasmid pPR17. The plasmid pIA7Δ4Δ1 ~1.3 kb EcoRI-BamHI restriction fragment contains part of Δ2 so therefore the construction restores Δ2 to Δ1. Plasmid pPR17 contains the ~0.9 kb PstI-HincII restriction fragment of bacteriophage λcI857 and thus blocks the lytic development of bacteriophage lambda in lysogenized host cells. In addition, plasmid pPR17 codes for and expresses the aforementioned trp E-insulin A chain fused gene product at levels significantly above that of other λcI gene containing plasmids known in the art. A restriction site and functional map of plasmid pPR17 is presented in FIG. 5 of the accompanying drawings.

The novel pPR17 recombinant plasmid can be transformed into $E.$ $coli$ such as, for example, $E.$ $coli$ K12 294 (disclosed in Goeddel et al., 1979, Proc. Nat. Acad. Sci. U.S.A. 76:106), $E.$ $coli$ K12 RV308 (disclosed in Mauer et al., 1980, J. Mol. Biol. 139:147–161), $E.$ $coli$ K12 C600 (disclosed in Bachman, 1972, Bacteriol. Rev. 36:526–557), $E.$ $coli$ K12 C600$R_k$- $M_k$- (disclosed in Chang and Cohen, 1974, Proc. Nat. Acad. Sci. 71:1030–1034), and the like, and then the resulting strains can be lysogenized with any bacteriophage λ which does not produce a functional cI repressor such as, for example, bacteriophage λcI90. Thus, the constructed strains $E.$ $coli$ K12 294λcI90/pPR17, $E.$ $coli$ K12 RV308λcI90/pPR17, $E.$ $coli$ K12 C600λcI90/pPR17 and $E.$ $coli$ K12 C600$R_k$-$M_k$-λIc90/pPR17 require retention of the pPR17 plasmid whereas constructed strains $E.$ $coli$ K12 294/pPR17, $E.$ $coli$ K12 RV308/pPR17, $E.$ $coli$ K12 C600/pPR17, and $E.$ $coli$ K12 C600$R_k$-$M_k$-/pPR17 survive equally well without the plasmid. A comparison of plasmid retention in the strains clearly demonstrates that substantially all the viable cells in the strains with the invention have the desired plasmid. Moreover, the $E.$ $coli$ K12 294λcI90/pPR17, $E.$ $coli$ K12 RV308λcI90/pPR17, $E.$ $coli$ K12 C600λcI90/pPR17, and $E.$ $coli$ K12 C600$R_k$-$M_k$-λcI90/pPR17 strains not only maintain the pPR17 plasmid, but also produce the desired fused gene product.

The improved selective system and usefulness of this invention can also be shown by cloning the plasmid pIB7Δ4Δ1 ~1.3 kb EcoRI-BamHI restriction fragment, which contains the trp E-insulin B chain gene, onto plasmid pPR12 in the manner described for plasmid pPR17. Plasmid pIB7Δ4Δ1 is derived from plasmid pBR322 in a way analogous to that described for pIA7Δ4Δ1. The construction of plasmid pIB7Δ4Δ1 is disclosed in Example 2 herein below.

Figure 6:
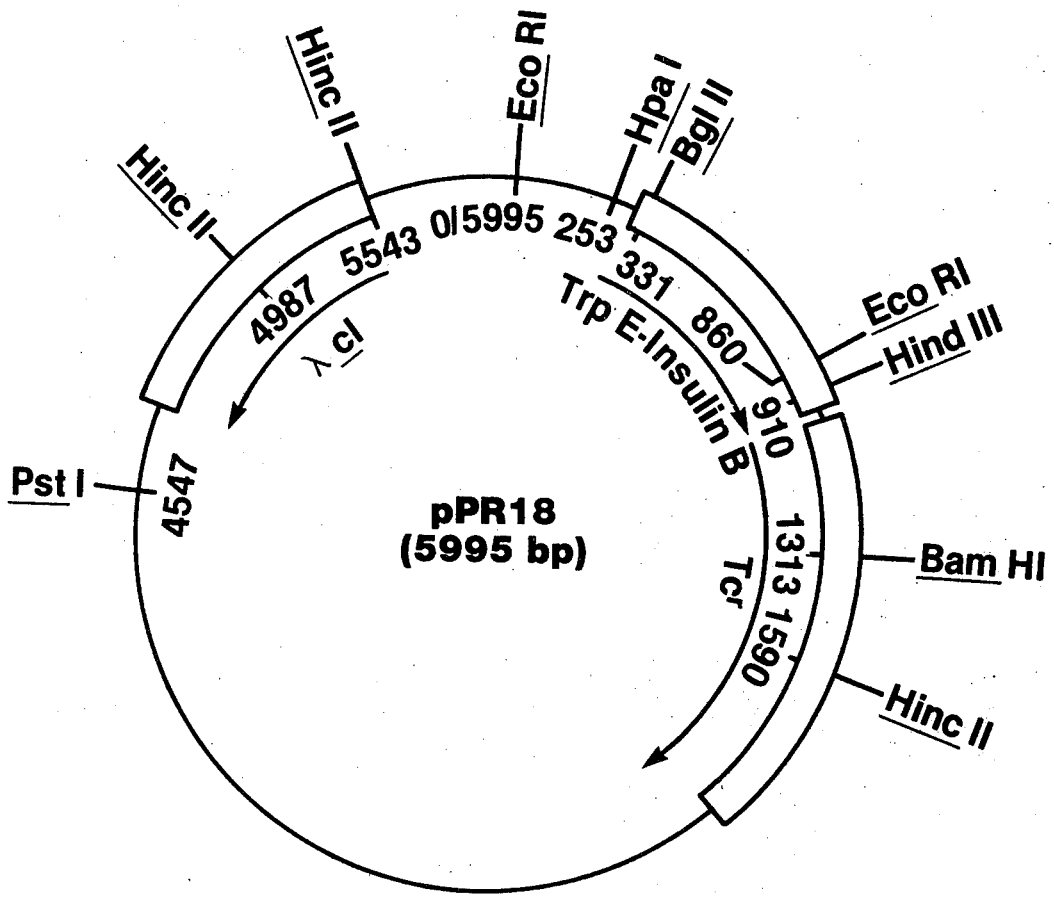

The cloning of the ~1.3 kb EcoRI-BamHI trp E-insulin B chain gene containing restriction fragment of plasmid pIB7Δ4Δ1 onto the ~4.7 kb EcoRI-BamHI restriction fragment of plasmid pPR12 results in the novel plasmid pPR18. Plasmid pPR18 contains the ~0.9 kb PstI-HincII restriction fragment of bacteriophage λcI857 and thus blocks the lytic development of bacteriophage lambda in lysogenized host cells. In addition, plasmid pPR18 codes for and expresses the aforementioned trp E-insulin B chain fused gene product at levels significantly above that of other λcI gene containing plasmids known in the art. A restriction site and functional map of plasmid pPR18 is presented in FIG. 6 of the accompanying drawings.

The novel pPR18 recombinant plasmid can be transformed into $E.$ $coli$ such as, for example, $E.$ $coli$ K12 294, $E.$ $coli$ K12 RV308, $E.$ $coli$ K12 C600, $E.$ $coli$ K12 C600$R_k$-$M_k$- and the like, and then the resulting strains can be lysogenized with any bacteriophage λ which does not produce a functional cI repressor such as, for example, bacteriophage λcI90. Thus, as was previously described for the lysogenized pPR17 containing strains, the constructed $E.$ $coli$ K12 294λcI90/pPR18, $E.$ $coli$ K12 RV308λcI90/pPR18, $E.$ $coli$ K12 C600λcI90/pPR18, and $E.$ $coli$ K12 C600$R_k$-$M_k$-λcI90/pPR18 strains require retention of the pPR18 plasmid whereas constructed strains $E.$ $coli$ K12 294/pPR18, $E.$ $coli$ K12 RV308/pPR18, $E.$ $coli$ K12 C600/pPR18, and $E.$ $coli$ K12 C600$R_k$-$M_k$-/pPR18 do not and survive equally well without the plasmid. A comparison of plasmid retention in the strains clearly demonstrates that substantially all the viable cells in the strains with the invention have the desired plasmid. Moreover, the $E.$ $coli$ K12 294λcI90/pPR18, $E.$ $coli$ K12 RV308λcI90/pPR18, $E.$ $coli$ K12 C600λcI90/pPR18, and $E.$ $coli$ K12 C600$R_k$-$M_k$-λcI90/pPR18 strains not only maintain their plasmids but also produce the desired fused gene product.

Novel plasmid pPR12 can also be transformed into a variety of host cells, such as, for example, $E.$ $coli$ K12 C600$R_k$-$M_k$-. The resulting strains can be lysogenized, as in the case of the plasmid pPR17 and pPR18 transformants, to produce strains that do not survive without the plasmid. Thus, constructed strain $E.$ $coli$ K12 C600$R_k$-$M_k$-λcI90/pPR12 requires retention of the pPR12 plasmid whereas constructed strain $E.$ $coli$ K12 C600$R_k$-$M_k$-/pPR12 survives equally well without the plasmid. A comparison of plasmid retention in the strains clearly demonstrates that substantially all the viable cells in the strain with the invention have the desired plasmid.

The λcI857 repressor gene used herein to illustrate the present invention is temperature sensitive and is inactivated at 38° C. to 44° C. or above. A temperature shift from 38° C., to 44° C. therefore lyses the cells by inducing the lytic cycle of the lambda prophage which, in accordance with the present invention, has been incorporated into the host cell strain. As is readily apparent, when a temperature sensitive repressor which represses a lethal or conditional lethal marker that causes host cell lysis is used and when the host cells are cultured at a temperature which inactivates the repressor and, in the case of a conditional lethal marker, at a temperature which is not within the temperature range for permissive culture of the host cells, the improved selection method of the present invention also provides a simple, convenient, and inexpensive procedure to lyse cells for purification of intracellular products.

As illustrated herein, the present invention employs a plasmid borne gene to repress a lethal chromosomal marker. Selection of cells is independent of the replicon and also the other genes on the plasmid and, although the preferred embodiment herein described employs the ~0.9 kb PstI-HincII CI containing restriction fragment of bacteriophage λcI857, the ~0.9 kb PstI-HincII cI containing restriction fragment of any other bacteriophage λ strain that produces a functional repressor can also be used. Furthermore, although the prophage used to exemplify the present invention carries a λcI90 mutation and thus does not produce a functional λcI repressor, other bacteriophage λ mutants can also be employed if they too lack a functional cI repressor gene.

As is readily apparent, such mutants require an alternate source of repressor to maintain the lysogenic state.

The selective method of the present invention allows for the enhanced expression of a functional polypeptide and can be imposed on host cells containing plasmid borne genes that express a variety of useful products. For example, the plasmid borne gene may be a naturally occurring gene, non-naturally occurring gene, or a gene which is in part naturally occurring and in part synthetic or non-naturally occurring. More particularly, the invention can be used to select and maintain cells containing a plasmid borne gene coding for human pre-proinsulin, human proinsulin, human insulin A-chain, human insulin B-chain, human growth hormone, non-human growth hormone, nonhuman insulin, human interferon, nonhuman interferon, viral antigen, urokinase, any peptide hormone, any enzyme, any polypeptide, or for virtually any other gene with research or commercial value.

In the specific embodiments of the invention described herein, plasmid replication and expression of the gene product are determined respectively by the replicon from pMB1 (disclosed in Bolivar, 1979, Life Sci. 25:807-818) and by the trp promoter. Other replicons and promoters can also be used so long as they are functional in $E.\ coli$ K12 and are not sensitive to the particular repressor being used. It is understood that those skilled in the art know or readily can determine which replicons and promoters are functional in $E.\ coli$ K12 and which are not sensitive to a particular repressor. Examples of other replicons include but are not limited to replicons from ColE1, NR1, RK2, RK6, pSC101, RP1, RP4, F, and the like, including bacteriophage that replicate in $E.\ coli$ K12. Examples of other promoters include but are not limited to the lac promoter, lipoprotein promoter, ribosomal protein or RNA promoters, and virtually any other promoter. It is understood that other replicons and promoters can be constructed and will be apparent to those skilled in the art.

In addition to being the preferred host for bacteriophage λ, the wealth of genetic and biochemical information about $E.\ coli$ K12 makes it a convenient host cell for purposes of the present invention. Although the strain $E.\ coli$ K12 RV308 is most preferred, the invention is not limited to any one genus, species, or strain, but can be used with any $E.\ coli$, coliform, or other cell in which bacteriophage λ is lysogenic and into which a functional repressor can be cloned.

All of the embodiments of the present invention share the common feature that they are insensitive to media composition. Therefore, the invention allows for a wide range of fermentation manipulation to improve productivity.

The following examples further illustrate and also present a preferred embodiment of the invention disclosed herein. Both an explanation of and the actual procedures for constructing the invention are described where appropriate.

EXAMPLE 1

Construction of Plasmid pIA7Δ4Δ1

A. Construction of Plasmid pBRHtrp

Plasmid pGM1 carries the $E.\ coli$ tryptophan operon containing the deletion ΔLE1413 (Miozzari, et al., 1978, $J.\ Bacteriology$, 1457-1466) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. $E.\ coli$ K12 W3110tna2trpΔ102/pGM1 has been deposited with the American Type Culture Collection (ATCC No. 31622) and pGM1 may be conventionally removed from the strain for use in the procedures described below.

About 20 μg. of the plasmid were digested with the restriction enzyme* PvuII which cleaves the plasmid at five sites. The gene fragments were next combined with EcoRI linkers (consisting of a self complementary oligonucleotide of the sequence: pCATGAATTCATG) providing an EcoRI cleavage site for later cloning into a plasmid containing an EcoRI site. The 20 μg of DNA fragments obtained from pGM1 were treated with 10 units T4 DNA ligase in the presence of 200 pico moles of the 5'-phosphorylated synthetic oligonucleotide pCATGAATTCATG and in 20 μl T4 DNA ligase buffer (20 mM tris, pH 7.6, 0.5 mM ATP, 10 mM MgCl$_2$, 5 mM dithiothreitol) at 4° C. overnight. The solution was then heated 10 minutes at 70° C. to halt ligation. The linkers were cleaved by EcoRI digestion and the fragments, now with EcoRI ends, were separated using 5 percent polyacrylamide gel electrophoresis (herein after "PAGE"). The three largest fragments were isolated from the gel by first staining with ethidium bromide and then locating the fragments with ultraviolet light and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 gm tris base, 5.5 gm boric acid, 0.09 gm Na$_2$EDTA in 1 liter H$_2$O). The aqueous solution was collected from the dialysis bag, phenol extracted, chloroform extracted, and made 0.2M with respect to sodium chloride. The DNA was then recovered in water after ethanol precipitation. The trp promoter/operator-containing gene with EcoRI sticky ends was identified in the procedure next described, which entails the insertion of fragments into a tetracycline sensitive plasmid which, upon promoter/operator insertion, becomes tetracycline resistant. All DNA fragment isolations hereinafter described are performed using PAGE followed by the electroelution method described above.

*Restriction and other enzymes can be readily obtained from the following sources:

Bethesda Research Laboratories Inc.
Box 6010
Rockville, Md. 20850

Boehringer Mannheim Biochemicals
7941 Castleway Drive
P.O. Box 50816
Indianapolis, Ind. 46250

Research Products
Miles Laboratories Inc.
Elkhart, Ind. 46515

B. Construction of Plasmid pBRH trp Expressing Tetracycline Resistance Under the Control of the Trp Promoter/Operator and Identification and Amplification of the Trp Promoter/Operator Containing DNA Fragment Isolated in 'A'above.

Plasmid pBRH1, (Rodriguez, et al., 1979, Nucleic Acids Research 6, 3267-3287) expresses ampicillin resistance and contains the gene for tetracycline resistance but, there being no associated promoter, does not express that resistance. The plasmid is accordingly tetracycline sensitive. By introducing a promoter/operator system in the EcoRI site, the plasmid can be made tetracycline resistant.

Plasmid pBRH1 was digested with EcoRI. The enzyme was removed by phenol extraction followed by chloroform extraction and then the DNA was recovered in water after ethanol precipitation. The resulting DNA molecule was, in separate reaction mixtures, combined with each of the three DNA fragments obtained in Example 1A above and ligated with T$_4$ DNA ligase as previously described. The DNA present in the reaction mixture was used to transform competent *E. coli* K12 strain 294, (Backman et al., 1976, Proc. Nat. Acad. Sci. USA 73:4174–4198, ATCC No. 31446) by standard techniques (Hershfield et al., 1974, Proc. Nat. Acad. Sci. USA 71:3455–3459) and the bacteria were then plated on LB plates (Miller, 1972) containing 20 µg/ml ampicillin and 5 µg/ml tetracycline.

Several tetracycline-resistant colonies were selected and the plasmid DNA was isolated and designated pBRHtrp. The presence of the desired fragment was confirmed by restriction enzyme analysis. Plasmid pBRH trp expresses β-lactamase, imparting ampicillin resistance, and contains a DNA fragment which includes the trp promoter/operator. The DNA fragment also codes for a first protein, (designated LE'), comprising a fusion of the first six amino acids of the trp leader and approximately the last third of the trp E polypeptide, a second protein (designated D'), corresponding to approximately the first half of the trp D polypeptide, and a third protein, coded for by the tetracycline resistance gene.

C. Construction of Plasmid pSOM7Δ2

Plasmid pBRHtrp was digested with EcoRI restriction enzyme and the resulting fragment, isolated by PAGE and electroelution, was combined with EcoRI-digested plasmid pSOM11 (Itakura et al., 1977, Sci. 198:1056, G. B. Patent Publication No. 2,007,676A). The mixture was ligated with T$_4$ DNA ligase and the resulting DNA transformed into *E. coli* K12 strain 294 as previously described. Transformant bacteria were selected on ampicillin-containing plates and the resulting ampicillin-resistant colonies were screened by colony hybridization (Gruenstein et al., 1975, Proc. Nat. Acad. Sci. USA 72:3951-3965). The trp promoter/operator-containing fragment, isolated from pBRH trp and then radioactively labelled with p$^{32}$, was used as a probe in the above procedure. Several colonies were shown to be positive by colony hybridization and were therefore selected. Plasmid DNA was isolated and the orientation of the inserted fragments was determined by restriction analysis, using enzymes BglII and BamHI in double digestion. Colonies containing the desired plasmid with the trp promoter/operator fragment in the proper orientation were grown in LB medium (Miller, 1972) containing 10 µg/ml ampicillin. The desired plasmid was designated pSOM7Δ2 and was used for subsequent constructions described below.

D. Construction of Plasmid pTrp24

1. Construction of a Gene Fragment Comprising Codons for the Distal Regions of the LE' Polypeptide With BglII and EcoRI Restriction Sites Respectively at the 5' and 3' Ends of the Coding Strand Plasmid pSOM7Δ2 was HindIII digested followed by digestion with lambda exonuclease (a 5' to 3' exonuclease) under conditions chosen so as to digest beyond the BglII restriction site within the LE' encoding region. About 20 µg of HindIII-digested pSOM7Δ2 was dissolved in buffer (20 mM glycine buffer, pH 9.6, 1mM MgCl$_2$, 1 mM β-mercaptoethanol). The resulting mixture was treated with 5 units of lambda exonuclease for 60 minutes at room temperature. The reaction mixture obtained was then phenol extracted, chloroform extracted, and ethanol precipitated.

To create an EcoRI residue at the distal end of the LE' gene fragment, a primer $^{32}$pCCTGTGCATGAT was synthesized by the improved phosphotriester method (Crea et al., 1978, Proc. Nat. Acad. Sci. USA 75: 5765) and hybridized to the single stranded end of the LE' gene fragment resulting from lambda exonuclease digestion. The hybridization was performed by dissolving 20 µg of the lambda exonuclease-treated HindIII digestion product of plasmid pSOM7Δ2 in 20 µl H$_2$O and combining with 6 µl of a solution containing approximately 80 picomoles of the 5'-phosphorylated oligonucleotide described above. The synthetic fragment was hybridized to the 3' end of the LE' coding sequence and the remaining single strand portion of the LE' fragment was filled in by Klenow Polymerase I using dATP, dTTP, dGTP and dCTP. Klenow Polymerase I is the fragment obtained by proteolytic cleavage of DNA Polymerase I. It contains the 5'→3' polymerizing activity, the 3'→5' exonucleolytic activity, but not the 5'→3' exonucleolytic activity of the parental enzyme (Kornberg, 1974, W. H. Freeman and Co., SFO, 98).

The reaction mixture was thus heated to 50° C. and let cool slowly to 10° C., whereafter 4 µl of Klenow enzyme were added. After 15 minutes incubation at room temperature, followed by 30 minutes incubation at 37° C., the reaction was stopped by the addition of 5 µl of 0.25 molar EDTA. The reaction mixture was phenol extracted, chloroform extracted, and ethanol precipitated. The DNA was subsequently cleaved with the restriction enzyme BglII and the fragments were separated by PAGE. An autoradiogram obtained from the gel revealed a $^{32}$p-labelled fragment of the expected length of approximately 470 bp, which was recovered by electroelution. As outlined, this fragment LE' (d) has a BglII terminus and a blunt end coinciding with the beginning of the primer.

2. Construction of Plasmid pThα1

Plasmid pThα1 was constructed by inserting a synthesized gene for thymosin alpha 1 into plasmid pBR322. The synthesis of the thymosin alpha 1 coding DNA involves the synthesis and subsequent ligation of the 16 oligonucleotides (T$_1$ through T$_{16}$) that are indicated by the double headed arrows in FIG. 7 of the accompanying drawings. A Met codon ATG was inserted at the N-terminus and the 5' ends were designed with single-stranded cohesive termini to facilitate joining to plasmids cleaved with EcoRI and BamHI. As can be readily appreciated, the BglII site in the center of the gene assists in the analysis of recombinant plasmids.

Oligodeoxyribonucleotides T$_1$ to T$_{16}$ were synthesized by the modified phosphotriester method using fully protected trideoxyribonucleotide building blocks (Itakura et al., 1977, Science 198:1056, and Crea et al., 1978). The various oligodeoxyribonucleotides are shown below in Table 1.

TABLE 1
SYNTHETIC OLIGONUCLEOTIDES FOR THYMOSINα1 GENE

| Compound | Sequence | Length | HPLC Analysis Retention Time (min)* |
|---|---|---|---|
| $T_1$ | A—A—T—T—C—A—T—G—T—C | 10 | 17.4 |
| $T_2$ | T—G—A—T—G—C—T—G—C—T—G—T—T—G—A | 15 | 24.3 |
| $T_3$ | T—A—C—T—T—C—T—T—C—T—G—A | 12 | 20.3 |
| $T_4$ | G—A—T—T—A—C—T—A—C—T—A—A—A | 13 | 22.0 |
| $T_5$ | G—C—A—G—C—A—T—C—A—G—A—C—A—T—G | 15 | 24.8 |
| $T_6$ | G—A—A—G—T—A—T—C—A—A—C—A | 12 | 20.1 |
| $T_7$ | A—G—T—A—A—T—C—T—C—A—G—A—A | 13 | 22.6 |
| $T_8$ | A—A—G—A—T—C—T—T—T—A—G—T | 12 | 20.2 |
| $T_9$ | G—A—T—C—T—T—A—A—G—G—A—A | 12 | 20.4 |
| $T_{10}$ | A—A—G—A—A—G—G—A—A—G—T—T | 12 | 21.1 |
| $T_{11}$ | G—T—C—G—A—A—G—A—G—G—C—T | 12 | 20.5 |
| $T_{12}$ | G—A—G—A—A—C—T—A—A—T—A—G | 12 | 20.4 |
| $T_{13}$ | C—T—T—C—T—T—C—T—C—C—T—T | 12 | 19.9 |
| $T_{14}$ | T—T—C—G—A—C—A—A—C—T—T—C | 12 | 20.5 |
| $T_{15}$ | G—T—T—C—T—C—A—G—C—C—T—C | 12 | 20.2 |
| $T_{16}$ | G—A—T—C—C—T—A—T—T—A | 10 | 17.2 |

*at ambient temperature

Figure 8:
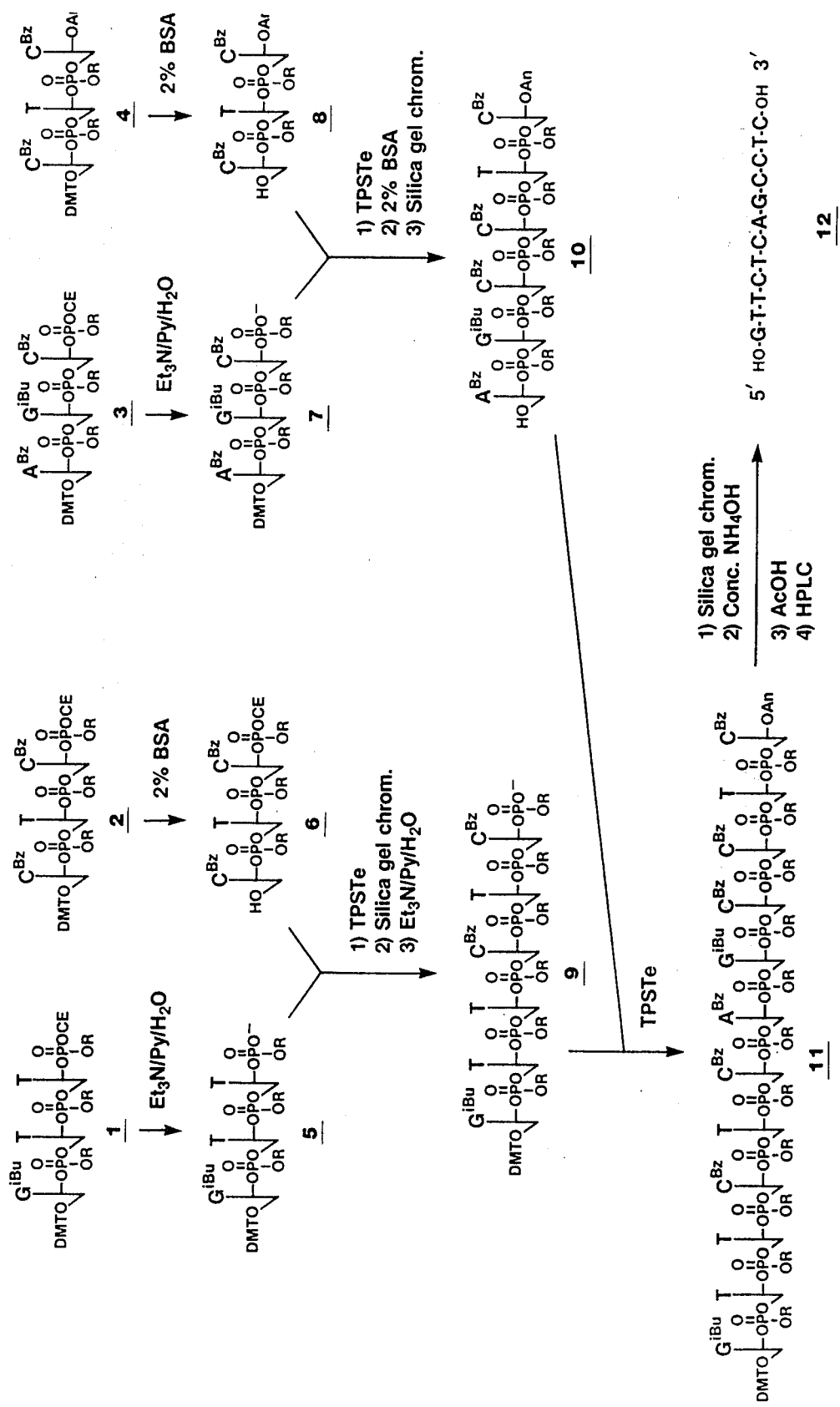

The above synthesis is typified by the following procedure for fragment $T_{15}$ as summarized in FIG. 8 of the accompanying drawings. Various nucleotide fragments that are used in the synthesis of $T_{15}$ are numerically designated in the Figure. The abbreviations employed are as follows: TPSTe, 2,4,6-triisopropylbenzenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; An, anisoyl; iBu, isobutryl; Py, pyridine; AcOH, acetic acid; Et$_3$N, triethylamine.

The fully protected trideoxyribonucleotides 4 (85 mg, 0.05 mmol) and 2 (180 mg, 0.1 mmol) were deblocked at the 5' hydroxyls by treatment with 2% BSA in 7:3 (v/v) chloroform/methanol (10 and 20 ml, respectively) for 10 minutes at 0° C. Reactions were stopped by addition of saturated aqueous ammonium bicarbonate (2 ml), extracted with chloroform (25 ml), and washed with water (2×10 ml). The organic layers were dried (magnesium sulfate), concentrated to small volumes (about 5 ml), and precipitated by addition of petroleum ether (35°–60° C. fraction). The colorless precipitates were collected by centrifugation and dried in a dessicator in vacuo to give 6 and 8, respectively, each homogeneous by silica gel tlc (Merck 60 F254, chloroform/methanol, 9:1).

Trimers 1 and 3 (270 mg, 0.15 mmol; 145 mg, 0.075 mmol) were converted into their phosphodiesters (5 and 7) by treatment with triethylamine/pyridine/water (1:3:1, v/v, 10 ml) for 25 minutes at ambient temperature. Reagents were removed by rotary evaporation and the residues dried by repeated evaporations with anhydrous pyridine (3×10 ml). Trimer 8 (0.05 mmol) and trimer 7 were combined with TPSTe (50 mg, 0.15 mmol) in anhydrous pyridine (3 ml) and the reaction mixture left in vacuo at ambient temperature for two hours. TLC analysis showed that 95% of the trimer 8 had been converted into hexamer product (visualized by detection of the DMT group by spraying with 10% aqueous sulfuric acid and heating at 60° C.). The reaction was quenched by addition of water (1.0 ml) and the solvent evaporated under reduced pressure. After removal of pyridine by coevaporations with toluene, the hexamer was deblocked at the 5' position with 2% BSA (8 ml) as described above for trimers 4 and 2. The product (10) was purified on a silica gel column (Merck 60 H, 3.5×5 cm) by step gradient elution with chloroform/methanol (98:2 to 95:5, v/v). Fractions containing product 10 were evaporated to dryness.

Similarly, trimer 5 was coupled to 6 and the fully protected product directly purified on silica gel. This latter compound was deblocked at the 3' end by triethylamine/pyridine/water as described above to give fragment 9.

Finally, hexamers 9 and 10 were coupled in anhydrous pyridine (2 ml) with TPSTe (75 mg, 0.225 mmol) as the condensing agent. Upon completion (4 hours, ambient temperature) the mixture was rotary evaporated and the residue chromatographed on silica gel. Product 11 (160 mg) was obtained by precipitation with petroleum ether and appeared homogeneous on TLC. A portion of compound 11 (20 mg) in pyridine (0.5 ml) was completely deblocked by treatment with concentrated ammonium hydroxide (7 ml, 8 hours, 60° C.) and subsequent treatment in 80% acetic acid (15 minutes, ambient temperature). After evaporation of acetic acid, the solid residue was dissolved in 4% aqueous ammonium hydroxide (v/v, 4 ml) and extracted with ethyl ether (3×2 ml). The aqueous phase was concentrated to 1–2 ml and a portion applied to HPLC for purification of 12. The fractions corresponding to the major peak were pooled (ca. 2.0 0.D.$_{254}$ units) and concentrated to about 5 ml. The final product 12 was desalted on Bio-gel P-2 (1.5×100 cm) by elution with 20% aqueous ethanol, reduced to dryness and resuspended in water (200 μl) to give a solution of A$_{254}$=10. The sequence of 12 was confirmed by two-dimensional sequence analysis.

Figure 9:
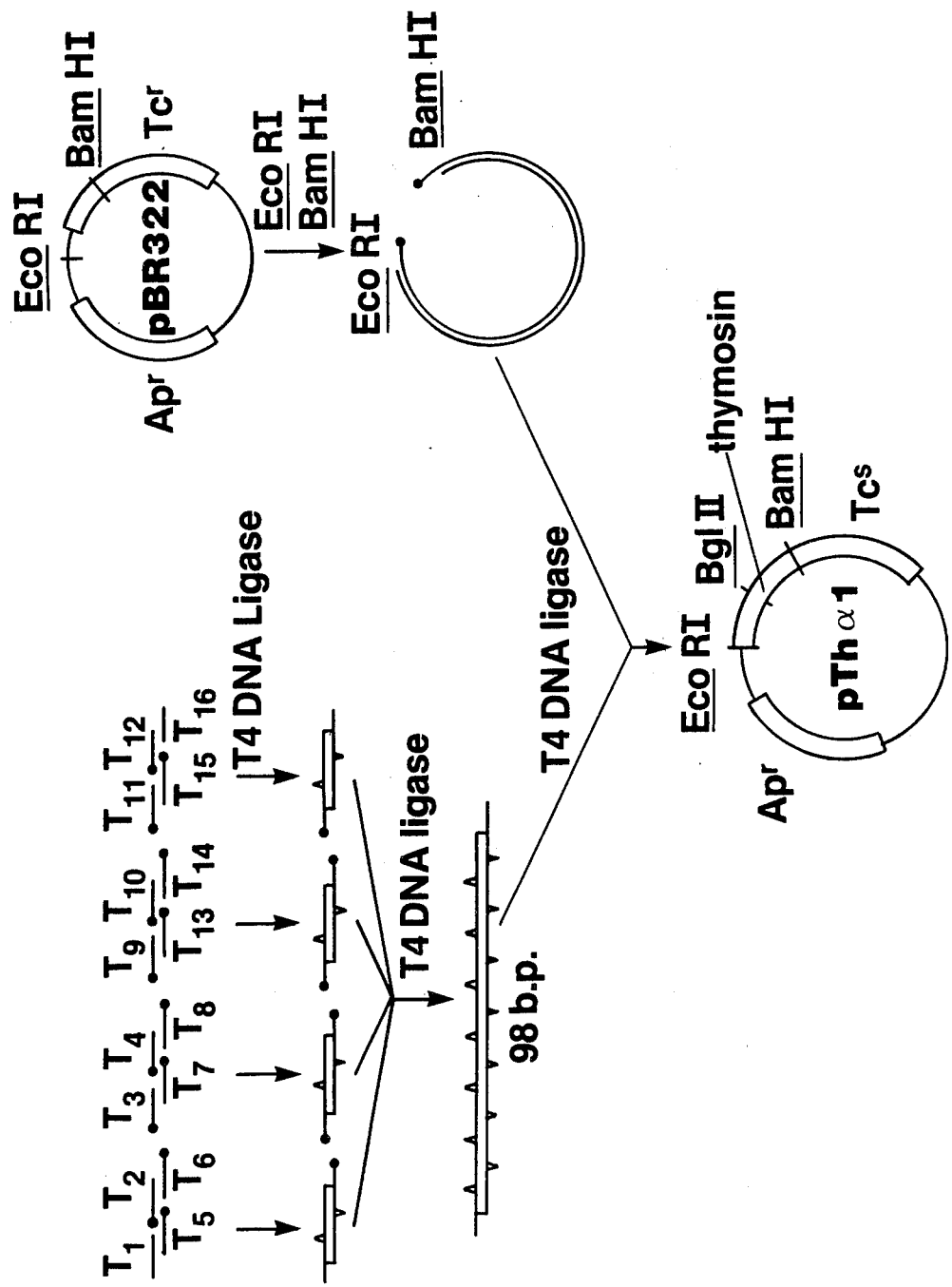

The complete thymosin alpha 1 gene was assembled from the 16 synthetic oligo-nucleotides by methods previously described in detail for somatostatin (Itakura et al., 1977), insulin (Goeddel et al., 1979), and growth hormone (Goeddel, Heyneker, et al., 1979, Nature 281:544). Ten microgram quantities of oligonucleotides $T_2$ through $T_{15}$ were quantitatively phosphorylated with [γ-$^{32}$P]-ATP (New England Nuclear) in the presence of $T_4$ polynucleotide kinase (Goeddel et al, 1979), to give specific activities of approximately 1 Ci/mmol. Radiolabelled fragments were purified by 20% polyacrylamide/7 M urea gel electrophoresis and sequences of the eluted fragments were verified by two-dimensional electrophoresis/homochromatography (Jay et al., 1974, Nucleic Acids Res. 1:331) of partial snake venom digests. Fragments T$_1$ and T$_{16}$ were left unphosphorylated to minimize undesired polymerization during subsequent ligation reactions. These oligonucleotides (2 μg each) were assembled in four groups of four fragments (see FIG. 9 of the accompanying drawings), by T$_4$ DNA ligase using published procedures (Goeddel et al., 1979). The reaction products were purified by gel electrophoresis on a 15% polyacrylamide gel containing 7 M urea (Maxam and Gilbert, 1977, Proc. Nat. Acad. Sci. USA 71:3455). The four isolated products were ligated together and the reaction mixture resolved by 10% polyacrylamide gel electrophoresis. DNA in the size range of the thymosin alpha 1 gene (90-105 base pairs) was electroeluted.

Plasmid pBR322 (0.5 μg) was treated with BamHI and EcoRI restriction endonucleases and the fragments separated by polyacrylamide gel electrophoresis. The large fragment was recovered from the gel by electroelution and subsequently ligated to the assembled synthetic DNA (Goeddel, Heyneker, et al., 1979). This mixture was used to transform E. coli K12 strain 294, ATCC No. 31446. Five percent of the transformation mixture was plated on LB plates containing 20 μg/ml ampicillin. The four ampicillin resistant colonies obtained were sensitive to tetracycline, suggesting insertion into the tetracycline resistance gene. Analysis of the plasmids from these four colonies showed that in each case the plasmid, designated pThα1, contained (a) a BglII site not found in pBR322 itself, thus indicating the presence of the thymosin alpha 1 gene as shown in FIG. 7, and (b) a fragment of approximately 105 base pairs generated by BamHI/EcoRI cleavage. The construction route for plasmid pThα1 (not drawn to scale), is presented in FIG. 9 of the accompanying drawings wherein the heavy dots indicate 5'-phosphate groups.

3. Reaction of Treated pThα1 and LE' (d) Fragment

The plasmid pThα1 contains a gene specifying ampicillin resistance and a structural gene specifying thymosin alpha 1 cloned at its 5' coding strand end into an EcoRI site and at its 3' end into a BamHI site. The thymosin gene contains a BglII site as well. To create a plasmid capable of accepting the LE' (d) fragment prepared above, pTHα1 was EcoRI digested followed by Klenow polymerase I reaction with dTTP and dATP to blunt the EcoRI residues. BglII digestion of the resulting product created a linear DNA fragment containing the gene for ampicillin resistance and, at its opposite ends, a sticky BglII residue and a blunt end. The resulting product could be recircularized by reaction with the LE' (d) fragment containing a BglII sticky end and a blunt end in the presence of T$_4$ ligase to form the plasmid pTrp24. In doing so, an EcoRI site is recreated at the position where blunt end ligation occurred.

E. Construction of Plasmid pSOM7Δ2Δ4

Successive digestion of pTrp24 with BglII and EcoRI, followed by PAGE and electroelution, yields a fragment having codons for the LE' (d) polypeptide with a BglII sticky end and an EcoRI sticky end adjacent to its 3' coding terminus. The LE' (d) fragment can be cloned into the BglII site of plasmid pSom7Δ2 to form an LE' polypeptide/somatostatin fusion protein expressed under the control of the tryptophan promoter/operator. To do so requires (1) partial EcoRI digestion of pSom7Δ2 in order to cleave the EcoRI site distal to the tryptophan promoter/operator, and (2) proper choice of the primer sequence in order to properly maintain the codon reading frame, and to recreate an EcoRI cleavage site.

Thus, 16 μg of plasmid pSom7Δ2 was diluted into 200 μl of buffer containing 20 mM Tris, pH 7.5, 5 mM MgCl$_2$, 0.02 NP40 detergent, and 100 mM NaCl, and treated with 0.5 units EcoRI. After 15 minutes at 37° C., the reaction mixture was phenol extracted, chloroform extracted, ethanol precipitated, and subsequently digested with BglII. The larger resulting fragment was isolated by the PAGE procedure followed by electroelution. This fragment contains the codons "LE' (p)" for the proximal end of the LE' polypeptide, ie, those upstream from the BglII site. This fragment was next ligated to the above LE' (d) fragment in the presence of T$_4$ DNA ligase to form the plasmid pSom7Δ2Δ4, which upon transformation into E. coli strain 294, efficiently produced a fusion protein consisting of the fully reconstituted LE polypeptide and somatostatin under the control of the tryptophan promoter/operator.

F. Construction of Linear DNA Having a PstI Residue at the 3' end and a BglII Residue at its 5' End Bounding a Gene Specifying Tetracycline Resistance Plasmid pBR322 was HindIII digested and the protruding HindIII ends were digested with S1 nuclease. The S1 nuclease digestion involved treatment of 10 μg of HindIII-cleaved pBR322 in 30 μl S1 buffer (0.3 M NaCl, 1 mM ZnCl$_2$, 25 mM sodium acetate, pH 4.5) with 300 units S1 nuclease for 30 minutes at 15° C. The reaction was stopped by the addition of 1 μl of 30 X S1 nuclease stop solution (0.8 M tris base, 50 mM EDTA). The mixture was phenol extracted, chloroform extracted, ethanol precipitated, and then EcoRI digested as previously described. The resulting fragment, obtained by the PAGE procedure followed by electroelution, has an EcoRI sticky end and a blunt end whose coding strand begins with the nucleotide thymidine. The S1-digested HindIII residue beginning with thymidine can be joined to a Klenow Polymerase I-treated BglII residue so as to reconstitute the BglII restriction site upon ligation.

Therefore plasmid pSOM7Δ2, prepared in Example 1C, was BglII digested and the resulting BglII sticky ends were made double stranded by treatment with Klenow Polymerase I using all four deoxynucleotide triphosphates. EcoRI cleavage of the resulting product, followed by PAGE and electroelution of the small fragment, yielded a linear piece of DNA containing the tryptophan promoter/operator and codons of the LE' "proximal" sequence upstream from the BglII site ("LE' (p)"). The product had an EcoRI end and a blunt end resulting from filling in the BglII site. However, the BglII site is reconstituted by ligation of the blunt end to the blunt end of the above S1-digested HindIII fragment. Thus, the two fragments were ligated in the presence of T$_4$ DNA ligase to form the recircularized plasmid pHKY10 which was propagated by transformation into competent E. coli strain 294 cells. Tetracycline resistant cells bearing the recombinant plasmid pHKY10 were selected and the plasmid DNA extracted. Digestion with BglII and PstI, followed by isolation by the PAGE procedure and electroelution of the large fragment, yielded the desired linear piece of DNA having PstI and BglII sticky ends. This DNA fragment, thus produced from pHKY10, contains the origin of replication and therefore is useful as a component in the construction of plasmid pIA7Δ4Δ1 in which both the genes coding for the trp LE' polypeptide fusion protein and the tetracycline resistance are controlled by the trp promoter/operator.

G. Construction of Linear DNA Having the Trp Promoter/Operator

Plasmid pSOM7Δ2Δ4, prepared in Example 1E, was subjected to partial EcoRI digestion followed by PstI digestion. The resulting fragment contained the trp promoter/operator and was isolated by the PAGE procedure followed by electroelution. Partial EcoRI digestion was necessary to obtain a fragment which was cleaved adjacent to the 5' end of the somatostatin gene but not cleaved at the EcoRI site present between the ampicillin resistance gene and the trp promoter/operator. Ampicillin resistance lost by the PstI cut in the ampicillin resistance gene can be restored upon ligation with the final pHKY10 linear DNA derivative produced in Example 1F above.

H. Isolation of the Insulin A Chain Structural Gene

The insulin A chain structural gene was obtained by the EcoRI and BamHI digestion of plasmid pIAl, whose construction is disclosed in Goeddel et al., 1979, Proc. Nat. Acad. Sci. USA 76:106. The desired fragment was purified by PAGE and electroelution and had EcoRI and BamHI termini.

I. Ligation of the Insulin A Chain Structural Gene, the Trp Promoter/Operator, and the pHKY10 Linear DNA Fragment Having PstI and BglII Termini The insulin A chain structural gene, the linear DNA fragment containing the trp promoter/operator (prepared in Example 1G), and the pHKY10 linear DNA fragment (prepared in Example 1F), were ligated together in proper orientation, as depicted in FIG. 1, to form the desired plasmid pIA7Δ4Δ1. Plasmid pIA7Δ4Δ1 can be readily selected because of the restoration of ampicillin and tetracycline resistance.

EXAMPLE 2

Construction of Plasmid pIB7Δ4Δ1

The desired plasmid was constructed in accordance with Example 1A-I except that the structural gene specifying the insulin B chain, rather than the insulin A chain, was used in the final ligation. The insulin B chain structural gene was obtained by the EcoRI and BamHI digestion of plasmid pIBl, whose construction is disclosed in Goeddel et. al., 1979. The insulin B chain encoding DNA fragment was purified by PAGE and electroelution and had EcoRI and BamHI termini.

Figure 2:
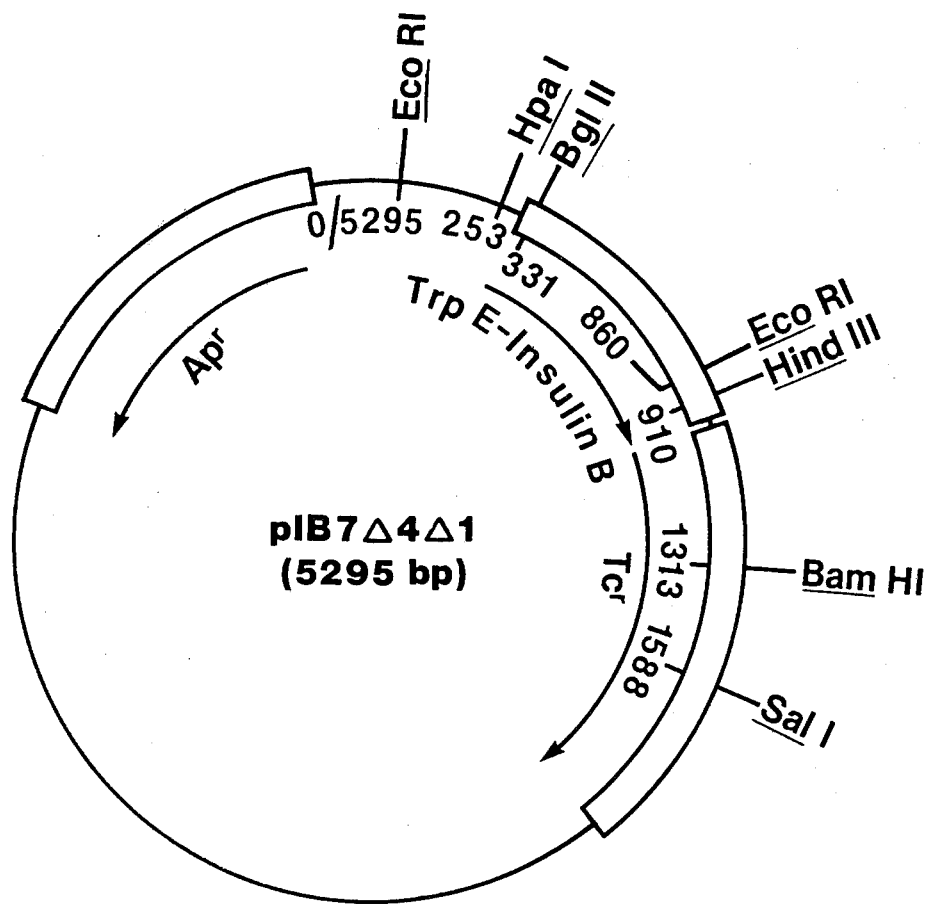
Figure 3:
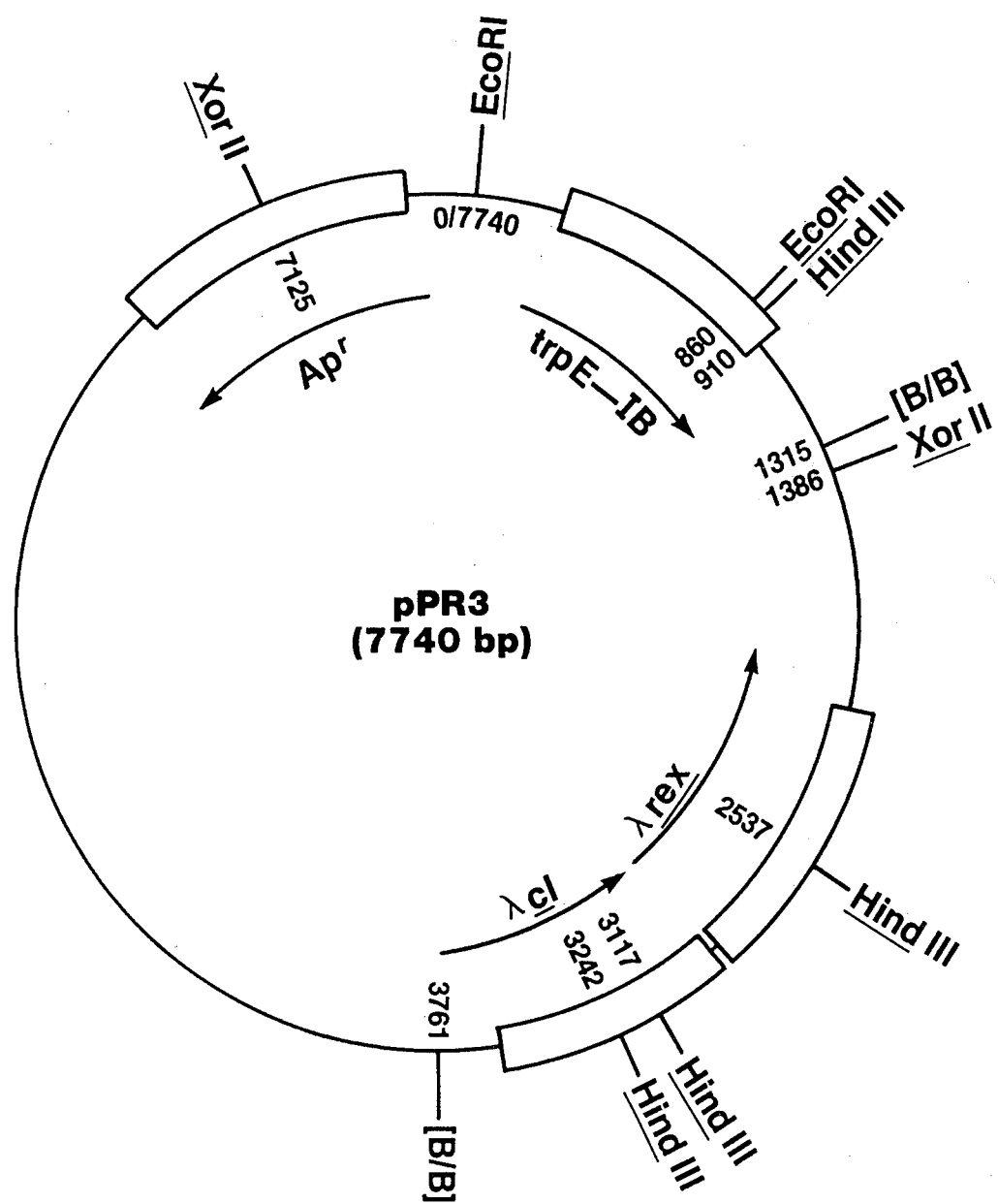
Figure 4:
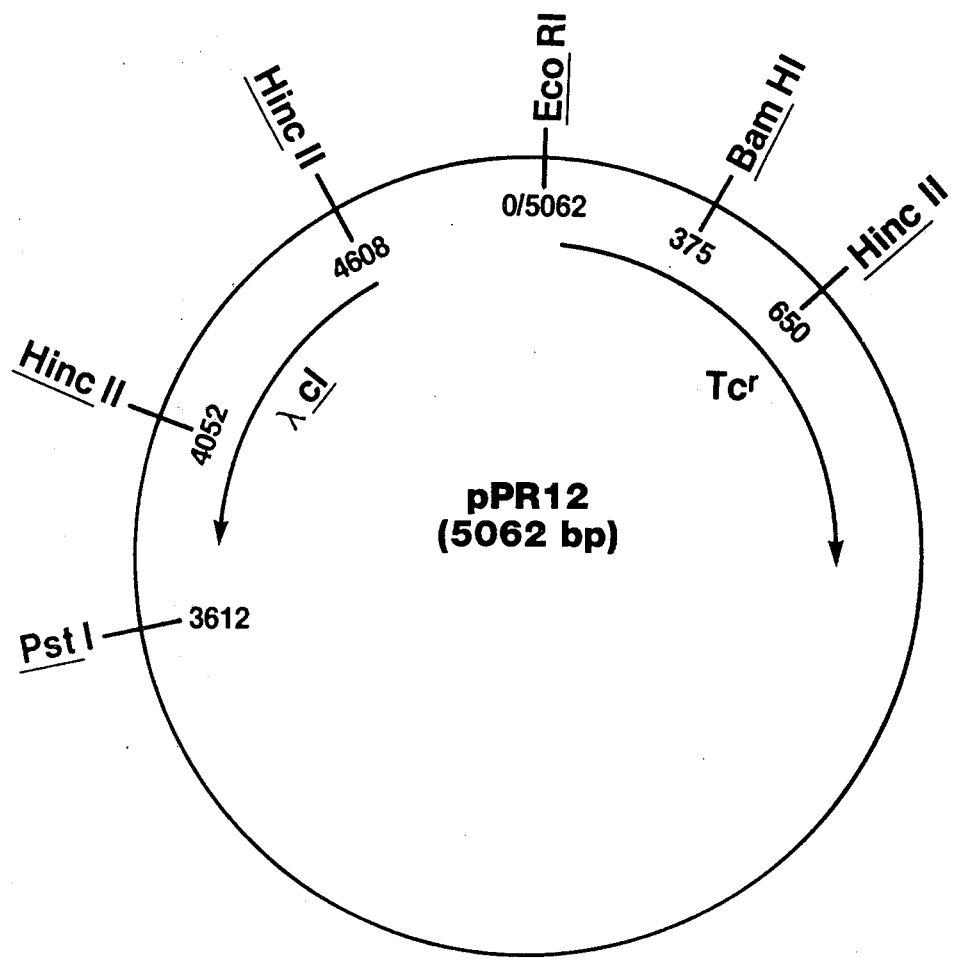

Plasmid pIB7Δ4Δ1 is depicted in FIG. 2 and can be readily selected because of the restoration of ampicillin and tetracycline resistance.

EXAMPLE 3

Construction of Plasmid pPR3

A. Isolation of a ~2.5 kb BglII Restriction Fragment of Bacteriophage λ Containing Genes For cI, rex, and Part of cro The several BglII restriction sites in bacteriophage λcI857 and a single BamHI restriction site in plasmid pIB7Δ4Δ1 allow for the cloning of bacteriophage fragments into the pIB7Δ4Δ1 cloning vector. Bacteriophage λcI857 contains six sites that are sensitive to BglII. One of the BglII fragments contains 2.5 kb including the λcI gene and also the λrex gene (Szybalski and Szybalski, 1979, Gene 7:217-280 and O'Brien, ed., March 1980, Genetic Maps, Vol. 1, NIH). BglII fragments contain 5' extensions with the sequence GATC that are complementary to 5' extensions on BamHI fragments. Human insulin plasmid, pIB7Δ4Δ1 contains a single site that is cleaved by BamHI. Cloning into the BamHI site inactivates the Tc resistance gene carried on pIB7Δ4Δ1. Ligation of BglII fragments and BamHI fragments produces recombinants with the sequences

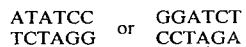

at the junctions. These sequences are not cleaved by BglII or BamHI. Therefore, restriction with both enzymes eliminates all ligation products except those containing a λBglII fragment ligated into the BamHI site of pIB7Δ4Δ1.

Restriction enzymes were purchased from commercial sources, disclosed in Example 1A, and were conventionally used according to known procedures. In addition, instructions are also supplied by the manufacturers. Thus, bacteriophage λcI857 sus S7 DNA was restricted to completion at 37° C. in a reaction mixture containing 100 μg. of DNA, 12 mM Tris.HCl, pH7.5, 12 mM MgCl2, 12 mM 2-mercaptoethanol and 100 units (in a volume of 1 ml.) of BglII restriction enzyme. The restriction fragments were separated by agarose gel electrophoresis (hereinafter "AGE"). The separated fragments were located in the gel by staining with ethidium bromide and visualizing fluorescent bands with an ultraviolet light. The ~2.5 kb fragment of interest was excised from the gel and electroeluted into TBE as taught in Example 1A. The aqueous solution was collected from the dialysis bag and passed over a DEAE Cellulose column *(0.5 ml. Whatman DE52) that had been equilibrated with equilibration buffer (0.1 M KCl, 10.0 mM Tris.HCl, pH 7.8). The column was washed with 2.5 ml. of equilibration buffer and the DNA (about 5 μg.) was eluted with 1.5 ml. of elution buffer (1 M NaCl, 10 mM Tris.HCl, pH 7.8). The eluent was adjusted to about 0.35 M with respect to Na+ ion concentration, and then the DNA was precipitated by addition 2 volumes (about 9 ml.) of 100% ethanol followed by cooling to −20° C. for 16 hr. The DNA precipitate was pelleted by centrifugation, washed with 75% ethanol, and dried. The DNA fragment isolations were performed by the AGE, electroelution, DEAE-Cellulose chromatography, and the ethanol precipitation procedure herein described. The DNA was redissolved in TE buffer (1 mM EDTA, 10 mM Tris.HCl, pH 7.8).

*DEAE cellulose column and DE52 can be obtained from Whatman Inc., 9 Bridewell Place, Clifton, N. J. 07014.

B. Digestion of Plasmid pIB7Δ4Δ1 with BamHI Restriction Enzyme

Plasmid pIB7Δ4Δ1 was restricted to completion at 37° C. in a 50 μl reaction mixture containing 20 mM Tris.HCl, pH 7.0, 100 mM NaCl, 7 mM MgCl2, 2 mM 2-mercaptoethanol, and 10 units of BamHI restriction endonuclease.

C. Ligation of the λcI Fragment with BglII Termini to the BamHI Digested pIB7Δ4Δ1

Ligation with T4 DNA ligase was performed in a 100 μl. reaction mixture containing about 1.4 μg. of the 2.5 kb BglII fragment (prepared in Example 3A), about 1.5 μg. of BamHI restricted pIB7Δ4Δ1 (prepared in Example 3B), 50 mM Tris.HCl, pH 7.8, 10 mM dithiothreitol, 5% glycerol, 10 mM MgCl$_2$, 0.1 mM ATP, and 0.1 unit of T4 DNA ligase. The reaction mixture was incubated at 4° C. for 18 hrs and then terminated by heating to 65° C. for 5 minutes. The thus prepared plasmid pPR3 was stored at 4° C. for future use.

EXAMPLE 4

Transformation of Plasmid PR3 Into *E. coli* K12 C600R$_K$-M$_K$-

Fresh overnight cultures of *E. coli* K12 C600R$_K$-M$_K$- (disclosed in Chang and Cohen, 1974, Proc. Nat. Acad. Sci. 71:1030-1034) were subcultured 1:10 in fresh L-broth (disclosed in Miller, 1972, Experiments in Molecular Genetics, Cold Spring Harbor Labs, Cold Spring Harbor, N.Y.) and grown at 37° C. for 1 hr. A total of 660 Klett units of cells were harvested, washed with 2.5 ml of 100 mM NaCl, suspended in 150 mM CaCl$_2$ with 10% glycerol, and incubated at room temperature for 20 min. The cells were harvested by centrifugation, resuspended in 0.5 ml of CaCl$_2$-glycerol, chilled on ice for 3-5 minutes and frozen. The suspensions of cells were stored in liquid nitrogen until use. Preservation and storage did not adversely affect the viability or frequency of transformation by covalently closed circular DNA. The cells were thawed in an ice bath and mixed in a ratio of 0.1 ml. of cells to 0.05 ml. of DNA (5 µl. pPR3 prepared according to the teaching of Example 3C and diluted with 45 µl. 0.1X SSC [standard saline citrate]). The samples thus prepared were chilled on ice for 20 minutes, heat shocked at 42° C. for 1 minute, chilled on ice for an additional 10 minutes, then diluted with 0.85 ml. of L-broth, incubated at 32° C. for 2 hr, spread on L-agar (disclosed in Miller, 1972) with about 1×10$^9$ each of λKH54hλ and λKH54h80 (both of which are disclosed in Backman et al. 1977, Science 196:182), and incubated at 32° C. Transformants were selected for immunity to bacteriophage λKH54hλ and λKH54h80 at 32° C. The recombinants were tested to verify Ap$^r$, Tc$^s$, λKH54hλ and λKH54h80 immunity at 32° C., and λKH54hλ and λKH54h80 sensitivity at 42° C. One transformant was selected and designated *E. coli* K12 C600R$_K$-M$_K$-/pPR3. This surviving colony was tested for the expected phenotypes and used for amplification and isolation of the constructed recombinant plasmid pPR3. Restriction enzyme analysis of plasmid pPR3 showed that the λrex, rather than the λcI, gene was closest to the trp E-insulin B chain gene.

EXAMPLE 5

Amplification and Isolation of Plasmid PR3

The plasmid DNA of *E. coli* K12 C600R$_K$-M$_K$-/pPR3 was amplified with chloramphenicol and isolated by cleared lysate procedure (disclosed in Bazaral and Helinski, 1968, J. Mol. Biol. 36:185-194). The covalently closed circular DNA was purified by equilibrium ultracentrifugation in CsCl and propidium di-iodide. The propidium di-iodide was extracted with 2-propanol and the DNA was stored in CsCl at −20° C. Working solutions of DNA were exchanged into SSC/10 buffer 0.015 M NaCl, 0.0015 M sodium citrate pH 7.0) by chromatography on Sephadex (PD10*) columns.

*Available from Pharmacia, 800 Centennial Ave, Piscataway, N.J. 08851.

EXAMPLE 6

Construction of Plasmid pPR12

A. Isolation of a λcI Gene Containing Linear DNA With PstI and HincII Termini

About 70 µg. of plasmid pPR3 (isolated in substantial accordance with the teaching of Example 5), were dissolved in 70 µl. 10X PstI buffer (200 mM Tris.HCl, pH 7.5, 100 mM MgCl$_2$, 500 mM (NH$_4$)$_2$SO$_4$), 50 µl. (1 mg./ml.) BSA (bovine serum albumin), and 555 µl. H$_2$O and then incubated at 65° C. for about 15 minutes. After about 25 µl. PstI (1 unit/µl.) restriction enzyme were added, the resultant mixture was incubated at 37° C. for about 4.5 hours. The resultant PstI restriction fragments were then conventionally isolated by AGE. Since there are two PstI restriction sites in plasmid pPR3, a complete PstI digestion results in a ~3.6 kb fragment and also a ~4.2 kb fragment. The latter fragment contains the bacteriophage λcI gene of interest. Therefore, the ~4.2 kb fragment was recovered as described herein above. The resultant DNA pellet, which comprises the desired ~4.2 kb restriction fragment, was suspended in 50 µl. TE buffer. The DNA suspension was then incubated at 65° C. for 15 minutes and then stored at 4° C. for future use.

About 50 µl. of the ~4.2 kb PstI restriction fragment (prepared above), 10 µl. 10X HincII buffer (100 mM Tris.HCl, pH 7.9, 600 mM NaCl, 66 mM MgCl$_2$, 10 mM dithiothreitol), 38 µl. H$_2$O, and 2 µl. (10 units/µl.) HincII restriction enzyme were incubated at 37° C. for about 20 minutes and then at 65° C. for about 5 minutes. After the mixture was cooled to about 20° C. and after about 200 µl. TBE were added, the restriction fragments were conventionally isolated by AGE. The desired ~0.9 kb PstI-HincII restriction fragment, which contained the bacteriophage λcI gene, was dissolved in 10 µl. TE buffer and stored at 4° C.

B. Isolation of a Replicon and tc$^r$ Gene Containing Linear DNA With HincII and PstI Termini About 100 µl. (3.2 µg) plasmid pBR322, 15 µl. 10X HincII buffer, 34 µl. H$_2$O, and 1 µl. (10 units/µl.) . of HincII restriction enzyme were incubated at 37° C. for about 20 minutes and then at 65° C. for about 5 minutes. The reaction mixture was then cooled to 4° C. and ethanol precipitated as taught in Example 3. The desired partial HincII digested pBR322 was suspended in a solution comprising 10 µl. 10X PstI buffer and 79 µl. H$_2$O and the resultant suspension was then incubated at 65° C. for 5 minutes followed by cooling to 4° C. Next, 10 µl. (1 mg./ml.) BSA and 2 µl. PstI (10 units/ml.) restriction enzyme were added. The resultant reaction mixture was incubated at 37° C. for 1 hour, then at 65° C. for 5 minutes, and finally cooled to 4° C. The thus prepared HincII-PstI restriction fragment was conventionally isolated by AGE. The DNA was dissolved in TE buffer and stored at 4° C. for future use.

C. Ligation of the Fragment With the λcI Gene and the Linear pBR322 DNA Fragment Having PstI and HincII Termini About 10 µl. (1.8 µg.) ~0.9 kb HincII-PstI fragment (prepared in Example 6B), and 10 µl. (~0.9 µg.) ~4 kb PstI-HincII fragment (prepared in Example 6A), were mixed and ethanol precipitated twice. The resultant DNA was dissolved in a solution of 2 µl. 5X ligation buffer (250 mM Tris.HCl, pH 7.8, 50 mM MgCl$_2$, 25 mM dithiothreitol, and 25% glycerol) and 4.67 μl. H$_2$O. After incubating the solution at 65° C. for 10 minutes, about 3 μl. 0.66 mM ATP and 0.33 μl. (2 units/μl.) T4 DNA ligase were added. The resultant ligation mixture was reacted at ambient temperature for 1.5 hours to produce the desired plasmid pPR12. The thus prepared plasmid pPR12 DNA was stored at 4° C. for future use.

EXAMPLE 7

Transformation of Plasmid pPR12 Into *E. coli* K12 C600R$_k$-M$_k$-

The desired transformation was carried out in substantial accordance with the teaching of Example 4 except that plasmid pPR12, rather than plasmid pPR3, was used. Transformants were selected for immunity to bacteriophage λKH54hλ and λKH54h80 at 32° C. The recombinants were tested to verify Ap$^s$, Tc$^r$, λKH54hλ and λKH54h80 immunity at 32° C., and λKH54hλ and λKH54h80 sensitivity at 42° C. One transformant was selected and designated *E. coli* K12 C600R$_k$-M$_k$-/pPR12. This surviving colony was tested for the expected phenotypes and used for amplification and isolation of the plasmid pPR12.

EXAMPLE 8

Amplification and Isolation of Plasmid pPR12

The desired amplification and isolation of plasmid pPR12 was carried out in substantial accordance with the teaching of Example 5.

EXAMPLE 9

Construction of Plasmid pPR17

A. Isolation of the ~4.7 kb EcoRI-BamHI Linear Fragment of Plasmid pPR12 Containing the λcI Gene and the Replicon About 150 μl. (20 μg.) of plasmid pPR12 DNA (prepared in Example 8), 20 μl. 10X BamHI buffer (200 mM Tris.HCl, pH 7.0, 1 M NaCl, 70 mM MgCl$_2$, 20 mM 2-mercaptoethanol), 2 μl. (20 units/μl.) BamHI restriction enzyme, and 28 μl. H$_2$O were incubated at 37° C. for 30 minutes, then at ambient temperature for 1.3 hours, and finally at 65° C. for 5 minutes. After the reaction mixture was cooled to 4° C., about 4 μl. (10 units/μl.) of EcoRI restriction enzyme were added. The resultant mixture was then incubated at 37° C. for 1 hour thus producing the desired ~4.7 kb restriction fragment. After conventional isolation by AGE, the desired DNA pellet was suspended in TE buffer and then stored at −4° C. for future use.

B. Isolation of the ~1.3 kb EcoRI-BamHI Linear Fragment of Plasmid pIA7Δ4Δ1 Containing the Gene for a Fusion Polypeptide of trp 1' E' and A Chain of Human Insulin The desired isolation was carried out in substantial accordance with the teaching of Example 9A except that plasmid pIA7Δ4Δ1, rather than plasmid pPR12, was used. In addition, the EcoRI restriction enzyme was reacted for only about ½ hour since only a partial EcoRI digestion was desired. After conventional isolation by AGE, the desired ~1.3 kb EcoRI-BamHI restriction fragment was used immediately in the ligation procedure disclosed below.

C. Ligation of the Insulin Fused Gene and the Linear pPR12 DNA Fragment Having EcoRI and BamHI Termini About 1.5 μg. of the ~4.7 kb DNA containing solution of Example 9A and 1.5 μg. of the ~1.3 kb DNA containing mixture of Example 9B were mixed and ethanol precipitated twice. The pellet was dissolved in a solution comprising 6 μl. H$_2$O and 2 μl. 5X ligation buffer and then incubated at 65° C. for 10 minutes. After the incubation, the mixture was cooled to 15° C. and then about 2 μl. 0.66 mM ATP and 0.1 μl. (1 unit/μl.) T4 DNA ligase were added. The ligation reaction was carried out at 15° C. for about 18 hours producing the desired plasmid pPR17.

EXAMPLE 10

Transformation of Plasmid pPR17 Into *E. coli* K12 C600R$_k$-M$_k$-

The desired transformation was carried out in substantial accordance with the teaching of Example 4 except that plasmid pPR17, rather than plasmid pPR3, was used. Transformants were selected for immunity to bacteriophage λKH54hλ and λKH54h80 at 32° C. The recombinants were tested to verify Ap$^s$, Tc$^r$, λKH54hλ and λKH54h80 immunity at 32° C., and λKH54hλ and λKH54h80 sensitivity at 42° C. One transformant was selected and designated *E. coli* K12 C600R$_k$-M$_k$-/pPR17. This surviving colony was tested for the expected phenotypes and used for amplification and isolation of the plasmid pPR17.

EXAMPLE 11

Amplification and Isolation of Plasmid pPR17

The desired amplification and isolation of plasmid pPR17 was carried out in substantial accordance with the teaching of Example 5.

EXAMPLE 12

Construction of Plasmid pPR18

The desired construction was carried out in substantial accordance with the teaching of Example 9A–C except that plasmid pIB7Δ4Δ1, rather than plasmid pIA7Δ4Δ1, was used to generate the ~1.3 kb EcoRI-BamHI restriction fragment.

EXAMPLE 13

Transformation of Plasmid pPR18 Into *E. coli* K12 C600R$_k$-M$_k$-

The desired transformation was carried out in substantial accordance with the teaching of Example 4 except that plasmid pPR18, rather than plasmid pPR3, was used. Transformants were selected for immunity to bacteriophage λKH54hλ and λKH54h80 at 32° C. The recombinants were tested to verify Ap$^s$, Tc$^r$, λKH54hλ and λKH54h80 immunity at 32° C., and λKH54hλ and λKH54h80 sensitivity at 42° C. One transformant was selected and designated *E. coli* K12 C600R$_k$-M$_k$-/pPR18. This surviving colony was tested for the expected phenotypes and used for amplification and isolation of the plasmid pPR18.

EXAMPLE 14

Transformation of Plasmid pPR17 Into *E. coli* K12 294

Plasmids of the present invention are modified against the K-restriction system by transformation into *E. coli* K12 294. *E. coli* K12 294 is R$_k$-M$_k$+ so therefore, upon transformation, unmodified plasmid DNA becomes modified and resistant to restriction by strains with $R_k{}^+M_k{}^+$ specificity. Thus, E. coli K12 294 transformants are used for amplifying and isolating plasmids of the present invention for subsequent transformation into $R_k{}^+M_k{}^+$ E. coli strains. Such strains include, for example, E. coli K12 RV308.

The desired transformation was carried out in substantial accordance with the teaching of Example 4 except that E. coli K12 294, rather than E. coli K12 C600$R_k$-$M_k$-, and plasmid pPR17, rather than pPR3, were used. Transformants were selected for Tc$^r$. The recombinants were tested to verify Ap$^s$, Tc$^r$, immunity at 32° C. to λKH54hλ and λKH54h80 and sensitivity at 42° C. to λKH54hλ and λKH54h80. The transformants exhibited 100% genetic linkage of the putative plasmid borne markers. One transformant was selected and designated E. coli K12 294/pPR17. This colony was tested to verify the expected phenotypes and used for amplification and isolation of plasmid pPR17.

EXAMPLE 15

Amplification and Isolation of Plasmid pPR17

The desired amplification and isolation of plasmid pPR17 was carried out in substantial accordance with the teaching of Example 5 except that E. coli K12 294/pPR17 was used.

EXAMPLE 16

Transformation of Plasmid pPR18 Into E. coli K12 294

The desired transformation was carried out in substantial accordance with the teaching of Example 14 except that plasmid pPR18, rather than plasmid pPR17, was used.

EXAMPLE 17

Amplification and Isolation of Plasmid pPR18

The desired amplification and isolation of plasmid pPR18 was carried out in substantial accordance with the teaching of Example 5 except that E. coli K12 294/pPR18 was used.

EXAMPLE 18

Transformation of Plasmid pPR17 Into E. coli K12 RV308

The desired transformation was carried out in substantial accordance with the teaching of Example 14 except that plasmid pPR17 from Example 15 and E. coli K12 RV308 were used.

EXAMPLE 19

Transformation of Plasmid pPR18 Into E. coli K12 RV308

The desired transformation was carried out in substantial accordance with the teaching of Example 14 except plasmid pPR18 from Example 17 and E. coli K12 RV308 were used.

EXAMPLE 20

Construction of E. coli K12 RV308λcI90/pPR17 by Lysogenization with λcI90

E. coli K12 RV308/pPR17 (prepared according to the teaching of Example 18) was grown at 32° C. until 35 Klett units and was then transferred to 45° C. for 60 minutes. The cells were infected with λcI90 at an moe of 20 and incubated at 45° C. for 40 minutes. Colonies were grown at 32° C. on L-agar containing 10 μg./ml. tetracycline. The resulting E. coli K12 RV308λcI90/pPR17 colonies were tested to verify growth at 32° C. and sensitivity at 42° C.

EXAMPLE 21

Construction of E. coli K12 RV308λcI90/pPR18

The desired construction was prepared in substantial accordance with the teaching of Example 20 except that E. coli K12 RV308/pPR18 (prepared in Example 19), rather than E. coli K12 RV308/pPR17, was used.

EXAMPLE 22

Construction of E. coli K12 C600$R_k$-$M_k$-λcI90/pPR12

The desired construction was prepared in substantial accordance with the teaching of Example 20 except that E. coli K12 C600$R_k$-$M_k$-/pPR12 (prepared in Example 7), rather than E. coli K12 RV308/pPR17, was used.

Other representative strains which are constructed in accordance with the foregoing teaching include:

| Example No. | Name |
| --- | --- |
| 23 | E. coli K12 C600/pPR17 |
| 24 | E. coli K12 C600/pPR18 |
| 25 | E. coli K12 RV308/pPR12 |
| 26 | E. coli K12 RV308λcI90/pPR12 |
| 27 | E. coli K12 C600λcI90/pPR17 |
| 28 | E. coli K12 C600λcI90/pPR18 |
| 29 | E. coli K12 294λcI90/pPR17 |
| 30 | E. coli K12 294λcI90/pPR18 |
| 31 | E. coli K12 C600$R_k$—$M_k$—λcI90/pPR17 |
| 32 | E. coli K12 C600$R_k$—$M_k$—λcI90/pPR18 |

Method For Determining Stabilities of Host Cells Containing Recombinant Plasmids With and Without Selection The Tc$^r$ gene on the recombinant plasmids was employed to assay the frequency of cells containing the plasmids. Serial dilutions of culture were spread on L-agar and grown at 32° C. with and without 10 μg./ml. of tetracycline. The frequency of plasmid+ cells was taken as the ratio of tetracycline resistant colonies to the total number of colonies that grew on L-agar without tetracycline. Alternatively, the colonies on L-agar were replica plated to L-agar with 10 μg./ml. of tetracycline and grown at 32° C. The frequency of plasmid+ cells was taken as the ratio of tetracycline resistant colonies to the total number of colonies that grew on L-agar without tetracycline. The results are presented as percentages in Table 2 for strains E. coli K12 RV308/pIA7Δ4Δ1 and E. coli K12 RV308λcI90/pPR17, in Table 3 for strains E. coli K12 RV308/pIB7Δ4Δ1 and E. coli K12 RV308λcI90/pPR18, and in Table 4 for E. coli K12 C600$R_k$-$M_k$-/pPR12 and E. coli K12 C600$R_k$-$M_k$-λcI90/pPR12.

TABLE 2

| | Stabilities of Recombinant Plasmids | |
| --- | --- | --- |
| | Percentage of Plasmid Retention | |
| Number of Culture Doublings | E. coli K12 RV308/pIA7Δ4Δ1 | E. coli K12 RV308λcI90/pPR17 |
| 9 | 96 | 100 |
| 30 | 95 | 100 |

TABLE 3

Stabilities of Recombinant Plasmids

| Number of Culture Doublings | Percentage of Plasmid Retention | |
|---|---|---|
| | E. coli K12 RV308/pIB7Δ4Δ1 | E. coli K12 RV308λcI90/pPR18 |
| 9 | 96 | 100 |
| 30 | 79 | 100 |

TABLE 4

Stabilities of Recombinant Plasmids

| Number of Culture Doublings | Percentage of Plasmid Retention | |
|---|---|---|
| | E. coli K12 C600$R_k$—$M_k$—/pPR12 | E. coli K12 C600$R_k$—$M_k$—λcI90/pPR12 |
| 33 | 87 | 100 |

Results in Tables 2–4 clearly demonstrate the effectiveness of the present selective system for maintaining recombinant plasmids in bacterial populations. About 5 percent of the cells in the culture of E. coli K12 RV308/pIA7Δ4Δ1 and about 21 percent of the cells in the culture E. coli K12 RV308/pIB7Δ4Δ1 were plasmid minus after 30 culture doublings. None of the cells in the cultures of E. coli K12 RV308λcI90/pPR17 and E. coli K12 RV308λcI90/pPR18, that had the selective system in place, were plasmid minus. Moreover, the culture of E. coli K12 C600$R_k$-$M_k$-λcI90/pPR12 also showed excellent plasmid stability. Thus, 13% of the cells in the culture of E. coli K12 C600$R_k$-$M_k$-/pPR12 were plasmid minus after 33 culture doublings, while all of the cells in the culture of E. coli K12 C600$R_k$-$M_k$-λcI90/pPR12, that had the selective system in place, were plasmid plus.

None of the plasmids of the present invention showed any plasmid segregation. Thus, the present improved plasmids are further distinguished over those lacking the improvement by the absence of recombination with the prophage. In fact, not one plasmid minus colony has been observed after growth with the improved selective system in place.

We claim:

1. In the method for stabilizing and selecting host cells containing recombinant DNA in which host cells are transformed with a recombinant DNA cloning vector which contains both the ∼2.5 kb BglII cI repressor-containing restriction fragment of bacteriophage λ and a gene which expresses a functional polypeptide, and in which the transformed host cells are lysogenized with a lysogenic organism containing a marker which is lethal or conditionally lethal in the host cells but which is repressed in the transformed host cell by the repressor gene contained in the recombinant DNA cloning vector, an improvement wherein the improvement comprises:

transforming the host cells with a recombinant DNA cloning vector comprising
   (a) the PstI-HincII cI repressor-containing restriction fragment of bacteriophage λ; and
   (b) a gene which expresses a functional polypeptide;

subject to the limitation that the host cells are E. coli, the lysogenic organism is bacteriophage λ and the recombinant DNA cloning vector contains a replicon and a promoter which are not sensitive to the repressor, and subject to the further limitation, that when the transformed host cells are lysogenized with a lysogenic organism containing a gene which is conditionally lethal, the resulting host cells are cultured under restrictive conditions.

2. The method of claim 1 in which the recombinant DNA cloning vector is a plasmid.

3. The method of claim 1 in which the recombinant DNA cloning vector is a bacteriophage.

4. The method of claim 1 in which the gene which expresses a functional polypeptide is selected from the group of genes consisting of naturally occurring genes, non-naturally occurring genes, and genes which are in part naturally occurring and are in part synthetic or non-naturally occurring.

5. The method of claim 1 in which the gene which expresses a functional polypeptide is selected from the group consisting of genes coding for human insulin, human pre-proinsulin, human proinsulin, human insulin A-chain, human insulin B-chain, non-human insulin, human growth hormone, non-human growth hormone, human interferon, non-human interferon, viral antigen, urokinase, any polypeptide, and any peptide hormone or enzyme.

6. The method of claim 1 in which the cI repressor is cI857.

7. The method of claim 1 in which the lysogenic organism contains a bacteriophage λcI gene which does not produce a functional cI repressor.

8. The method of claim 7 in which the lysogenic organism is bacteriophage lambda cI90.

9. The method of claim 1 in which the lysogenic organism is bacteriophage λcI857.

10. The method of claim 1 in which the lysogenic organism has the cI gene deleted.

11. The method of claim 1 in which the host cells are E. coli.

12. The method of claim 11 in which the host cells are E. coli K12.

13. The method of claim 1 in which the recombinant DNA cloning vector is plasmid pPR17.

14. The method of claim 1 in which the recombinant DNA cloning vector is plasmid pPR18.

15. A recombinant DNA cloning vector which is a cloning vector of claim 1.

16. The recombinant DNA cloning vector of claim 15 which is plasmid pPR17.

17. The recombinant DNA cloning vector of claim 15 which is plasmid pPR18.

18. A host cell which is transformed with a recombinant DNA cloning vector of claim 15.

19. The transformed host cell of claim 18 which is E. coli.

20. The transformed lysogenized host cell of claim 1 which is E. coli K12 C600$R_k$-$M_k$-λcI90/pPR17.

21. The transformed lysogenized host cell of claim 1 which is E. coli K12 294λcI90/pPR18.

22. The transformed lysogenized host cell of claim 1 which is E. coli K12 RV308λcI90/pPR17.

23. The transformed lysogenized host cell of claim 1 which is E. coli K12 RV308λcI90/pPR18.

24. The recombinant DNA cloning vector of claim 15 which is plasmid pPR12.

25. A host cell transformed with the cloning vector of claim 24.

26. The transformed host cell of claim 25 which is E. coli K12 C600$R_k$-$M_k$-λcI90/pPR12.

27. The restriction fragment pPR12Δ2.

* * * * *